(12) United States Patent
Mie et al.

(10) Patent No.: US 7,700,718 B2
(45) Date of Patent: Apr. 20, 2010

(54) MATERIAL FOR PROMOTING THE FREEZING OF WATER OR HYDROUS SUBSTANCE

(75) Inventors: Yasuhiro Mie, Hokkaido (JP); Sakae Tsuda, Hokkaido (JP); Yoshiyuki Nishimiya, Hokkaido (JP); Fumio Mizutani, Hokkaido (JP)

(73) Assignee: National Institute of Advanced Industrial Science and Technology, Chiyoda-ku, Tokyo (JP)

( * ) Notice: Subject to any disclaimer, the term of this patent is extended or adjusted under 35 U.S.C. 154(b) by 497 days.

(21) Appl. No.: 11/635,058

(22) Filed: Dec. 7, 2006

(65) Prior Publication Data

US 2007/0134647 A1    Jun. 14, 2007

(30) Foreign Application Priority Data

Dec. 9, 2005  (JP) .............................. 2005-356674
Aug. 22, 2006 (JP) .............................. 2006-225536

(51) Int. Cl.
*C07K 14/46* (2006.01)
(52) U.S. Cl. .................................................. 530/324
(58) Field of Classification Search ........................ None
See application file for complete search history.

(56) References Cited

U.S. PATENT DOCUMENTS 4,784,943 A * 11/1988 Warren et al. .............. 435/7.32

FOREIGN PATENT DOCUMENTS

DE          100 60 746 A1    6/2001
EP          1 452 539 A1     9/2004
JP          2004-344033 A    12/2004
WO          WO 2004/065928 A2  8/2004

OTHER PUBLICATIONS

Jia and Davies ("Antifreeze proteins: an unusual receptor-ligand interaction," TRENDS in Biocehmical Sciences, 2002, 27, 101-106.*
Du et al. ("Ice nucleation inhibition," J. Biol. Chem., 2003, 278, 36000-36004.*
Margaritis et al. ("Principles and Biotechnological Applications of Bacterial Ice Nucleation," Critical Reviews in Biotechnology, 1991, 11, 277-295).*
Davies et al., Antifreeze Proteins, Current Opinion in Structural Biology, 7:828-834 (1997).
Hew et al., Protein Interaction With Ice, European Journal of Biochemistry, 203:33-42 (1992).
R. E. Feeney; "Inhibition and Promotion of Freezing: Fish Antifreeze Proteins and Ice-Nucleating Proteins"; XP 000571887; Comments Agric. & Food Chemistry; 1988; pp. 147-181; vol. 1 No. 3; Gordon and Breach Publishers; Langhorne, PA, USA.

* cited by examiner

*Primary Examiner*—Cecilia Tsang
*Assistant Examiner*—Christina Bradley
(74) *Attorney, Agent, or Firm*—Sughrue Mion, PLLC (57) ABSTRACT

A novel material having ice nucleation activity or activity to promote freezing is provided. The present invention related to a carrier upon which polypeptides are immobilized for promoting the freezing of water or a hydrous substance. That is a carrier upon which polypeptides having side chains for binding to water molecules on the molecular surfaces of the polypeptides are integrated and immobilized; and a carrier upon which antifreeze proteins are integrated and immobilized.

6 Claims, 3 Drawing Sheets

MATERIAL FOR PROMOTING THE FREEZING OF WATER OR HYDROUS SUBSTANCE

BACKGROUND OF THE INVENTION

1. Field of the Invention

The present invention relates to a material for promoting the freezing of water or a hydrous substance, a carrier on which antifreeze proteins are immobilized, a method for promoting the freezing of water or a hydrous substance, a method for freezing water or a hydrous substance while removing gases contained therein, and a method for freezing a water component in a hydrous substance while concentrating components other than water in the hydrous substance.

2. Background Art

It is generally thought that water freezes at 0° C. However, water does not freeze at or lower than 0° C. (supercool state), unless a trigger substance for freezing, that is, an "ice nucleus," is present. To naturally cause the generation of ice nuclei within water or a hydrous substance in a supercool state and thus cause the freezing thereof, such a substance must be cooled to a low temperature between −20° C. (general freezer temperature) and −196° C. (liquid nitrogen temperature), for example. Meanwhile, when ice nuclei are caused to be present, water or a hydrous substance can be frozen at a high temperature of 0° C. or lower. Examples of known ice nucleus substances, that is, substances that promote freezing, include silver iodide and ice nucleation-active bacteria, which enable the freezing of water at −8° C. and temperatures between −4 and −2° C., respectively. In particular, large amounts of cooling energy consumption is a problem in technical fields including the manufacturing industry, the processing industry, the freezing industry, the ice-making industry, the thermal preservation industry, food preservation, cell preservation, organ preservation, rainmaking, and artificial snowfall. Hence, the use of ice nucleus substances in the relevant technical fields has been expected. Specifically, the freezing of water with low energy (at high temperatures of 0° C. or lower) through the use of ice nucleus substances has been expected. However, the use of the above-described ice nucleus substances results in the presence of a mixture of heavy metals and bacteria in a hydrous substance. There is concern that this adversely affects the environment, human bodies, the ecosystem, and the like. Furthermore, applicable fields and ranges are extremely limited because of cost (ice nucleation-active bacteria are relatively expensive) and the like. Therefore, development of a new material that can function as an ice nucleus and can exert activity to promote the freezing of water has been strongly desired.

Moreover, when water is frozen by a general method, cloudy (milky) ice is generally formed because of the effects of air and the like dissolved in water. In the meantime, regarding ice to be used for beverages (e.g., beverages with water, beverages "on the rocks," and cool drinks), food preservation, decorative ice cylinders, or the like, ice with a low impurity level and high clarity is thought to be suitable because of its difficulty in thawing, its high beauty, and its ability to evoke a refreshingly cool feeling. Because of a rising trend toward cleanliness in recent years, ice-making apparatuses or the like with which clear ice can be produced are increasingly incorporated not only in ice-makers for business use but also in household refrigerators. Conventional clear ice production methods are: a method that involves freezing by spraying hot air from the top surface of an ice tray at a predetermined angle; a method that involves freezing in turn starting from the lower surface of an ice tray using a Peltier element; a method that involves supplying water to an ice tray and then vibrating the ice tray; a method that involves degassing dissolved gases such as air in water before ice making; a method that involves lowering an opening of an ice tray, supplying water in the form of a fountain, and then gradually freezing an ice making container (from the side thereof to the whole container); and a method that involves sending cool air to the back of an ice tray and then freezing while heating using a heater embedded in the cover of the ice tray, and the like. Specifically, temperature control for water to be frozen or an ice-making container, complicated tasks such as degassing or extrusion of water, and apparatuses and related costs have been required for clear ice production. Furthermore, large quantities of cooling energy at around −20° C. have been required for freezing. Hence, development of a new method for conveniently producing clear ice at a low cost and with low energy has been strongly desired.

Furthermore, an example of technology using water freezing is freeze concentration technology. This technology is a method that involves partially freezing a hydrous substance to separate water in the form of ice, so as to concentrate a solute. The technology has major advantages over other concentration methods, such that it enables uniform concentration of a solute component and has a high ability to preserve the qualities of a solute. It is expected to apply the freeze concentration technology to concentration (e.g., for liquid foods, medicines, or liquid fuel) and to clarification treatment or wastewater treatment (e.g., for waste water or waste liquid). Various apparatuses for such applications have been developed. However, all of these apparatuses have mechanisms by which a liquid to be treated is frozen by supercooling. Hence, the apparatuses are problematic in that solutes are easily incorporated in ice, the resulting concentration rates are low, and the energy efficiencies are poor. The apparatuses are also problematic in that a concentration unit with multiple stages must be provided because of the low concentration rate of a concentration unit with a single stage. This results in higher priced, more complicated, and larger apparatuses. Moreover, a freezing machine has been required for every concentration unit, so that large quantities of energy have been required for obtaining frozen products. Accordingly, development of a new technique capable of conveniently freezing and concentrating a target at low cost with low energy but without requiring supercooling has been strongly desired.

An antifreeze protein is relatively a small protein comprising a polypeptide of approximately 30 to 150 residues. It is known that an antifreeze protein is capable of inhibiting the freezing of water or a hydrous substance by binding to a specific crystal surface of an ice nucleus so as to suppress the ice crystal growth within a temperature range of 0° C. or lower. In recent years, the structures of various antifreeze proteins have been revealed by an NMR method or an X-ray crystal structure analysis method, so that their sites for binding to ice crystals have been revealed (Davies P. L. and Sykes B. D. 1997. Curr. Opin. Struct. Biol. 7: 828-834).

In the meantime, an ice nucleation protein is a protein that promotes the ice crystal growth. For example, an ice nucleation protein derived from *Pseudomonas syringae*, which is a kind of ice nucleation bacteria, is a membrane protein comprising approximately 1200 amino acids and being composed of 3 regions: an N-terminal region (up to 19 kDa); a central region (up to 94 kDa); and a C-terminal region (up to 7 kDa). Of these 3 regions, the central region is composed of a characteristic repeating amino acid sequence, and the sequence is thought to be a site that exerts ice nucleation activity (Hew C. L. and Yang D. S. C., 1992. Eur. J. Biochem. 203: 33-42).

An antifreeze protein and an ice nucleation protein share no homology in terms of amino acid sequence. Furthermore, the molecular weight of an ice nucleation protein is 10 to 20 or more times larger than that of an antifreeze protein.

In general, an antifreeze protein is stable and can be easily extracted from organisms containing the protein (JP Patent Publication (Kokai) No. 2004-344033 A) or easily obtained using a genetic engineering technique. On the other hand, no technology for stably isolating and purifying an ice nucleation protein in a large amount has been developed. Hence, it is extremely difficult to apply a pure ice nucleation protein as a material for promoting the freezing of water.

SUMMARY OF THE INVENTION

An object of the present invention is to provide a novel material having ice nucleation activity or activity to promote freezing. Another object of the present invention is to provide a method for conveniently producing clear ice at low cost with low energy and a method for implementing freeze concentration.

As a result of intensive studies to achieve the above objects, the present inventors have discovered that through integration and immobilization of polypeptides having side chains for binding to water molecules on the molecular surfaces of the polypeptides on a carrier or through integration and immobilization of antifreeze proteins on a carrier, such substances can be caused to act as ice nucleus substances. The present inventors have also discovered that by using such substances water or a hydrous substance can be frozen while removing gases or components other than water, such as solutes contained in such water or hydrous substance. Thus the present inventors have completed the present invention.

The present invention encompasses the following inventions.

(1) A carrier upon which polypeptides are immobilized for promoting the freezing of water or a hydrous substance, wherein polypeptides having side chains for binding to water molecules on the molecular surfaces of the polypeptides are integrated and immobilized on the carrier.

(2) The carrier upon which polypeptides are immobilized according to (1), wherein the polypeptides are oriented and immobilized on the carrier so that the side chains for binding to water molecules are exposed.

(3) The carrier upon which polypeptides are immobilized according to (1) or (2), wherein the polypeptides are immobilized in an amount between $1 \times 10^{-13}$ and $1 \times 10^{-9}$ mol/cm$^2$.

(4) A carrier upon which antifreeze proteins are immobilized, wherein antifreeze proteins are integrated and immobilized on a carrier.

(5) The carrier upon which antifreeze proteins are immobilized according to (4), wherein the antifreeze proteins are oriented and immobilized on the carrier so that the sites for binding to ice crystals are exposed.

(6) The carrier upon which antifreeze proteins are immobilized according to (4) or (5), wherein the sites for binding to ice crystals of the antifreeze proteins form a plane structure.

(7) The carrier upon which antifreeze proteins are immobilized according to any one of (4) to (6), wherein the antifreeze proteins are type III antifreeze proteins.

(8) The carrier upon which antifreeze proteins are immobilized according to any one of (4) to (7), wherein the antifreeze proteins are antifreeze proteins into which cysteine has been introduced and the cysteine-introduced antifreeze proteins are immobilized on the carrier via the thiol group of cysteine.

(9) The carrier upon which antifreeze proteins are immobilized according to any one of (4) to (8), wherein the antifreeze proteins are immobilized in an amount between $1 \times 10^{-13}$ and $1 \times 10^{-9}$ mol/cm$^2$.

(10) A method for promoting the freezing of water or a hydrous substance, which is carried out by causing the carrier upon which polypeptides are immobilized according to any one of (1) to (3) or the carrier upon which antifreeze proteins are immobilized according to any one of (4) to (9) to come into contact with water or a hydrous substance.

(11) A method for freezing water or a hydrous substance while removing a gas contained in the water or the hydrous substance, which is carried out by causing the carrier upon which polypeptides are immobilized according to any one of (1) to (3) or the carrier upon which antifreeze proteins are immobilized according to any one of (4) to (9) to come into contact with the water or the hydrous substance.

(12) A method for freezing a water component in a hydrous substance while concentrating components other than water in the hydrous substance, which is carried out by causing the carrier upon which polypeptides are immobilized according to any one of (1) to (3) or the carrier upon which antifreeze proteins are immobilized according to any one of (4) to (9) to come into contact with the hydrous substance.

According to the present invention, a safe material having high ice nucleation activity and high activity to promote freezing is provided, with which water or a hydrous substance can be frozen at a high temperature of 0° C. or lower. Furthermore, according to the present invention, water (water component) can be frozen while gases dissolved in water or a hydrous substance are removed or while components other than water in a hydrous substance are concentrated.

The present specification encompasses contents described in the specification and/or drawings of Japanese Patent Application No. 2005-356674 and No. 2006-225536 that serves as a basis for the priority of the present application.

DETAILED DESCRIPTION OF THE PREFERRED EMBODIMENTS

The present inventors have discovered that, when polypeptides having side chains for binding to water molecules on the molecular surfaces of the polypeptides are integrated and immobilized on a carrier, and the carrier is caused to come into contact with water or a hydrous substance, the freezing of water or a hydrous substance is promoted, freezing of water or a hydrous substance proceeds while gases contained therein are removed, and freezing of a hydrous substance also proceeds while components other than water in a hydrous substance are concentrated.

Therefore, in an embodiment, the present invention relates to a carrier upon which polypeptides are immobilized for promoting the freezing of water or a hydrous substance, wherein polypeptides having side chains for binding to water molecules on the molecular surfaces of the polypeptides are integrated and immobilized on a carrier. The carrier upon which polypeptides are immobilized can also be used for freezing water or a hydrous substance while dissolved gases are removed and/or for freezing water (or a water component) while components other than water in a hydrous substance are concentrated.

Such polypeptides having side chains for binding to water molecules on the molecular surfaces of the polypeptides are polypeptides wherein amino acid residues having such side chains for binding to water molecules are exposed on the molecular surfaces within the three-dimensional molecular structures. In the present invention, polypeptides include peptides, oligopeptides, and proteins.

Examples of amino acid residues having side chains for binding to water molecules include amino acid residues having polar groups in their side chains, such as serine, threonine, cysteine, tyrosine, asparagine, glutamine, lysine, histidine, arginine, aspartic acid, and glutamic acid.

Examples of the above polypeptides to be immobilized on a carrier include oxidoreductase such as glucose, transferase such as aminotransferase, hydrolytic enzymes such as lipase, lyase such as catalase, isomerase such as glucose phosphate isomerase, globular proteins such as myoglobin, structural proteins such as keratin, amino acid synthase, membrane proteins, metal proteins, antimicrobial proteins, immune proteins, photoreceptor proteins, glycoproteins, molecular motors, DNA-binding proteins, and antifreeze proteins.

The phrase "polypeptides are integrated and immobilized on a carrier" means that a plurality of polypeptide molecules are densely immobilized on a carrier. Polypeptides are immobilized on a carrier in an amount preferably between $1\times10^{-13}$ and $1\times10^{-9}$ mol/cm$^2$, and more preferably between $1\times10^{-12}$ and $1\times10^{-10}$ mol/cm$^2$.

Polypeptides are preferably oriented and immobilized on a carrier, so that their side chains for binding to water molecules are exposed. This enables integration of side chains for binding to water molecules being exposed on the carrier surface. Hence, a carrier upon which polypeptides are immobilized having high ice nucleation activity and high activity to promote freezing can be obtained. The phrase " . . . oriented, so that their side chains . . . are exposed" means that side chains for binding to water molecules are oriented so as to facilitate their contact with water or a hydrous substance; that is, it means that the side chains are oriented facing the outside of the carrier. A method for orienting and immobilizing polypeptides on a carrier is described later.

In the present invention, "ice nucleation activity" means activity by which ice nuclei are formed through promotion of gathering multiple water molecules, thus causing ice crystal growth to begin. "Activity to promote freezing" means activity to raise the freezing temperature (freezing point) of water or a hydrous substance. Such freezing temperature can be measured by gradually lowering the temperature of water or a hydrous substance and then observing temperatures at which the water or the hydrous substance freezes. When water or a hydrous substance freezes while undergoing sublimation, the freezing temperature can be measured by observing both freezing and sublimation.

As polypeptides having side chains for binding to water molecules, antifreeze proteins are preferably immobilized on a carrier. Antifreeze proteins have sites for binding to ice crystals, and such sites contain amino acid residues having side chains for binding to water molecules.

Therefore, in an embodiment, the present invention relates to a carrier upon which antifreeze proteins are immobilized, wherein antifreeze proteins are integrated and immobilized on a carrier. The antifreeze proteins integrated and immobilized on the carrier have ice nucleation activity and activity to promote freezing. Hence, when the carrier upon which antifreeze proteins are immobilized of the present invention is caused to come into contact with water or a hydrous substance, the freezing of the water or the hydrous substance can be promoted.

An antifreeze protein is known as an in vivo biophylaxis substance of fish or the like, which specifically binds to the surfaces of ice crystals formed within cells within a freezing temperature range so as to suppress the ice crystal growth and thus protect the body (specifically, tissues) from freezing. In the present invention, examples of such antifreeze protein include peptides, oligopeptides, polypeptides, and proteins having antifreeze activity; that is, activity of inhibiting ice crystal growth. Furthermore, examples of the antifreeze proteins in the present invention include protein types where polypeptide chains are modified with sugar chains; that is, antifreeze glycoproteins (AFGPs). Examples of antifreeze proteins include those derived from fish, fungi (fungi or bacteria), insects, or plants. Examples of fish having antifreeze proteins include fish species of the genera *Zoarces, Myoxocephalus, Gymnocanthus, Hemilepidotus, Furcina, Hypomesus, Spirinchus, Mallotus, Pleurogrammus, Sebastes, Clupea, Limanda, Liopsetta, Clidoderma, Cleisthenes, Microstomus, Lepidopsetta, Platichthys, Kareius, Eopsetta, Gadus, Theragra, Ammodytes, Hypoptychus, Trachurus, Brachyopsis, Pholis, Opisthocentrus, Ascoldia*, and *Pholidapus*.

Examples of fungi (fungi or bacteria) having antifreeze proteins include *Bacillus globisporus* of the genus *Bacillus*, *Candida* sp. and *Candida scottii* of the genus *Candida*, *Cladosporium herbarum* of the genus *Cladosporium*, fungi of the order Aphyllophorales, fungi of the order Agaricales, fungi of the order Cantharellales, bacteria of the genus *Flavobacterium*, bacteria of the genus *Pseudomonas*, and bacteria of the genus *Micrococcus*.

Examples of insects having antifreeze proteins include insects of the family Tortricidae, insects of the family Tenebrionidae, and insects of the genus *Dorcus*.

Examples of plants having antifreeze proteins include plant species of the families Brassicaceae, Gramineae, Plantaginaceae, Aceraceae, Oxalidaceae, Cyperaceae, Asteraceae, Apocynaceae, Ranunculaceae, Caprifoliaceae, Violaceae, Apiaceae, Polygonaceae, Ericaceae, Solanaceae, Caryophyllaceae, Hydrophyllaceae, Polemoniaceae, Rosaceae, Geraniaceae, Buddlejaceae, Fagaceae, Pinaceae, Leguminosae, Oleaceae, Salicaceae, and Liliaceae.

These antifreeze proteins may be used independently, or antifreeze proteins derived from a plurality of species may be used in combination.

The antifreeze activity of antifreeze proteins is evaluated as activity of causing thermal hysteresis, inhibition of ice crystal growth, or inhibition of ice recrystallization in water or a hydrous substance to which the antifreeze proteins are added.

Alternatively, the antifreeze activity of a subject protein can also be evaluated by observing ice crystal shapes under a microscope, since ice crystals in a characteristic shape (e.g., in the case of an antifreeze protein derived from fish, a bipyramid-type ice crystal formed of two stacked pyramids on the bottom surface) are formed in a hydrous substance wherein such antifreeze protein is present.

In general, the freezing point of water and the melting point of ice are the same. In the presence of antifreeze proteins, the proteins bind to ice crystal surfaces so as to suppress the ice crystal growth and thus to strongly suppress the binding between ice crystals, resulting in a difference between the freezing point of water and the melting point of ice. This phenomenon is referred to as thermal hysteresis. The intensity of the antifreeze activity of antifreeze proteins is generally evaluated based on a difference between the melting point of ice and the freezing point of water due to the presence of the antifreeze proteins. The difference between the melting point and the freezing point can be evaluated as thermal hysteresis activity. Thermal hysteresis activity can be measured using an osmometer or a microscope with a freezing stage. Furthermore, formed ice crystals grow by absorbing water generated as a result of sublimation or partial thawing at a relatively high temperature of −10° C. or higher. Inhibition of ice recrystallization means an effect of inhibiting this phenomenon.

The phrase "antifreeze proteins are integrated and immobilized on a carrier" means that a plurality of antifreeze proteins are densely immobilized on a carrier, similarly to the above. Antifreeze proteins are immobilized on a carrier at a density preferably between $1\times10^{-13}$ and $1\times10^{-9}$ mol/cm$^2$ and more preferably between $1\times10^{-12}$ and $1\times10^{-10}$ mol/cm$^2$.

Antifreeze proteins to be immobilized on a carrier are preferably those with sites for binding to ice crystals that form a plane structure. When antifreeze proteins with sites for binding to ice crystals that form a plane structure are integrated and immobilized on a carrier, a huge surface for binding to ice crystals is formed. It is thought that the surface promotes the gathering of multiple water molecules, following which the formation of ice nuclei and ice crystal growth are promoted, resulting in high ice nucleation activity and high activity to promote freezing.

Moreover, antifreeze proteins used herein are preferably derived from fish and particularly preferably derived from fish of the genus *Zoarces* because of their high activity, availability, cost effectiveness, and the like.

Antifreeze proteins derived from fish are classified based on their structures into 4 types (type I to type IV) and a type having a sugar chain (antifreeze glycoprotein: abbreviated as "AFGP"). Type I antifreeze protein is characterized by its high Ala content and forms an α-helix structure wherein Thr and Asp residues are arranged at regular intervals. Type II antifreeze protein is characterized by its high Cys content (8%) and forms a structure analogous to that of the sugar-chain recognition region of type C lectin. Type III antifreeze protein forms a globular structure characterized by its double-helix-like structural motif. Type IV antifreeze protein is characterized by its high Gln residue content and is inferred to have an α-helix bundle structure. An antifreeze glycoprotein comprises a repeating unit of 3 residues (-Ala-Thr-Ala-) and is characterized in that the Thr residue is modified with a sugar chain. The molecular weight of type I antifreeze protein is approximately between 3,000 and 4,500, that of type II antifreeze protein is approximately 20,000, that of type III antifreeze protein is approximately 7,000, that of type IV antifreeze protein is approximately 11,000, and that of the antifreeze glycoprotein is approximately between 2,600 and 33,000. All of these antifreeze proteins have amphiphilic properties and also have the property of being lysed at high concentrations in water regardless of type, such as type I, type II, or AFGP.

Antifreeze proteins to be used in the present invention may be of any types, including types I to IV and AFGP. Antifreeze proteins of type II and type III are preferably used. The sites for binding to ice crystals of type II and type III antifreeze proteins derived from fish form plane structures. Hence, such antifreeze proteins that are integrated have high ice nucleation activity and high activity to promote freezing.

Alternatively, it is also known that the sites for binding to ice crystals of antifreeze proteins derived from insects form plane structures. Thus, such antifreeze proteins derived from insects are preferably used in the present invention.

A specific example of a preferable antifreeze protein is an antifreeze protein comprising the amino acid sequence of SEQ ID NO: 2. A protein that is functionally equivalent to the protein comprising the amino acid sequence of SEQ ID NO: 2 can also be used as a preferable antifreeze protein. "Functionally equivalent" means that a subject protein has biological functions or biochemical functions (that is, antifreeze activity) equivalent to that of the protein comprising the amino acid sequence of SEQ ID NO: 2.

An example of a protein that is functionally equivalent to the protein comprising the amino acid sequence of SEQ ID NO: 2 is a protein comprising an amino acid sequence derived from the amino acid sequence of SEQ ID NO: 2 by deletion, substitution, insertion, or addition of 1 or several amino acids and having antifreeze activity. "Several amino acids" means generally 2 to 10, preferably 2 to 5, and more preferably 2 to 3 amino acids.

An example of a protein that is functionally equivalent to the protein comprising the amino acid sequence of SEQ ID NO: 2 is a protein comprising an amino acid sequence that shares at least 50% or more identity, preferably 75% or more identity, further preferably 85% or more identity, further more preferably 90% or more identity, and particularly preferably 95% or more identity with the amino acid sequence of SEQ ID NO: 2 and having antifreeze activity.

The identity of an amino acid sequence can be determined by a method that is generally employed in the technical field, such as algorithm BLAST according to Karlin and Altschul (Proc. Natl. Acad. Sci. U.S.A. 90: 5873-5877, 1993). Based on this algorithm, a program referred to as BLASTN or BLASTX has been developed (Altschul et al. J. Mol. Biol. 215: 403-410, 1990). Specific techniques for these analysis methods are known (http://www.ncbi.nlm.nih.gov).

Antifreeze proteins can be purified from fish, fungi (fungi or bacteria), insects, plants, or the like by a method known in the technical field.

For example, when antifreeze proteins are obtained from fish blood, blood is collected using a syringe from an antifreeze protein-producing fish body via its tail vein, and then the blood is allowed to stand at around 4° C. for 12 hours or longer. The blood cell component (containing no antifreeze proteins) precipitated by this procedure is gently removed (decantation) so as not to rupture erythrocyte membranes. The remaining serum component (containing antifreeze proteins) is subjected to generally employed biochemical separation procedures such as dialysis, ion exchange chromatography, HPLC chromatography, or the like, so that the antifreeze proteins can be obtained (Schrag, J. D. et al, Biochim. Biophys. Acta, 915, 357-370 (1987)).

When antifreeze proteins are obtained from fish muscle, antifreeze protein-producing fish bodies are crushed using a mixer, either directly or after removal of their heads and organs, thereby preparing fish paste. Water or a buffer is added to the fish paste and the fish paste is then suspended well therein. At this time, a paste suspension is heated at 50 to 90° C., if necessary (particularly, when type I and type II antifreeze proteins are purified). The paste suspension is allowed to stand or is subjected to centrifugation at 3,000 rpm to 12,000 rpm for approximately 30 minutes, thereby obtaining a supernatant solution. The solution is subjected to a generally employed biochemical separation procedure such as dialysis, ion exchange chromatography, or HPLC chromatography, so that antifreeze proteins can be obtained (JP Patent Publication (Kokai) No. 2004-083546 A).

For example, when antifreeze proteins are obtained from fungi (fungi or bacteria), they are cultured in medium, microbial bodies are separated from the culture solution, and then the antifreeze protein is collected, thereby producing antifreeze proteins. For separation of microbial bodies, centrifugation, filtration, ultrafiltration, or the like can be employed, for example. Antifreeze proteins contained in a culture supernatant solution obtained after separation of microbial bodies can be isolated and purified by a salting out method using ammonium sulfate, sodium sulfate, or the like, an organic solvent precipitation method using acetone or ethanol, a column chromatography method using cation exchangers, anion exchangers, or the like, or a gel filtration method using agarose derivatives or the like, for example.

Furthermore, with the use of the above amino acid sequence or disclosed amino acid sequence information, an antifreeze protein can be synthesized by a technique known in the technical field, such as a carrier peptide synthesis method. Moreover, an antifreeze protein can also be produced by a known gene recombination technique using the information pertaining to the DNA encoding the antifreeze protein. In addition, the nucleotide sequence of the DNA encoding the protein comprising the amino acid sequence of SEQ ID NO: 2 is shown in SEQ ID NO: 1. The production of an antifreeze protein using a recombination technique will be described below.

A recombinant vector for production of an antifreeze protein can be obtained by ligating the nucleotide sequence of the above DNA or the nucleotide sequence of a disclosed cDNA to an appropriate vector. A transformant can be obtained by introducing such recombinant vector for production of an antifreeze protein into a host, so that the antifreeze protein can be expressed.

Vectors used herein are phages or plasmids that are autonomously replicable within host microorganisms. Examples of a plasmid DNA include a plasmid derived from *Escherichia coli* (e.g., pET21a, pGEX4T, pUC118, pUC119, pUC18, or pUC19), a plasmid derived from *Bacillus subtilis* (e.g., pUB110 or pTP5), and a plasmid derived from yeast (e.g., YEp13, YEp24, or YCp50). Examples of a phage DNA include λ phage (e.g., λ gt11 or λ ZAP). Furthermore, vectors of animal viruses such as the Vaccinia virus or vectors of insect viruses such as Baculovirus can also be used.

An example of a method that is employed for insertion of an antifreeze protein cDNA into a vector involves cleaving a purified DNA with an appropriate restriction enzyme, inserting the product into a restriction enzyme site or a multicloning site of an appropriate vector DNA, and then ligating the resultant to the vector.

Furthermore, in addition to a promoter and an antifreeze protein cDNA, a cis element such as an enhancer, splicing signal, polyA addition signal, a selection marker, a ribosome binding sequence (SD sequence), or the like may be ligated to a recombinant vector for the production of an antifreeze protein, which is used in mammalian cells, if desired.

For ligation of a DNA fragment to a vector fragment, known DNA ligase is used. After annealing of the DNA fragment and the vector fragment for ligation, a recombinant vector for production of an antifreeze protein is then constructed.

Hosts to be used for transformation are not particularly limited, as long as they can express antifreeze proteins. Examples of such hosts include bacteria (e.g., *Escherichia coli* or *Bacillus subtilis*), yeast, animal cells (e.g., COS cells or CHO cells), and insect cells.

As an example, when a bacterium is used as a host, a recombinant vector for production of an antifreeze protein is preferably autonomously replicable within the bacterium and comprises a promoter, a ribosome binding sequence, an antifreeze protein DNA, and a transcription termination sequence. Moreover, a gene that controls a promoter may also be contained. An example of *Escherichia coli* is *Escherichia coli* BL21. An example of *Bacillus subtilis* is *Bacillus subtilis*. Any promoter may be used, as long as it can be expressed in a host such as *Escherichia coli*. Methods for introducing recombinant vectors into bacteria are not particularly limited. Examples of such method include a method using calcium ions and an electroporation method.

When yeast, animal cells, insect cells, and the like are used as hosts, antifreeze proteins can be produced similarly according to techniques known in the technical field.

Antifreeze proteins can be obtained by culturing the above-prepared transformants and then harvesting the proteins from the culture product. "Culture product" means any of culture supernatants, cultured cells, cultured microbial cells, disrupted cells, and disrupted microbial bodies. A method for culturing the above transformants in medium is performed according to a method generally employed for culturing hosts.

As a medium for culturing transformants obtained using microorganisms such as *Escherichia coli* or yeast cells as hosts, either a natural or a synthetic medium may be used, as long as it contains carbon sources, nitrogen sources, inorganic salts, and the like, is assimilable by microorganisms, and enables efficient culture of transformants.

Culture is generally carried out under aerobic conditions such as shake culture or aeration and agitation culture at 37° C. for 6 to 24 hours. During a culture period, a roughly neutral pH is maintained. pH is adjusted using inorganic or organic acid, alkaline solution, or the like. During culture, antibiotics such as ampicillin or tetracycline may be added to the medium, if necessary.

After culture, when antifreeze proteins are produced within the microbial bodies or within cells, the proteins are extracted by disrupting the microbial bodies or cells. Furthermore, when antifreeze proteins are produced outside the microbial bodies or outside the cells, the culture solution is directly used or the microbial bodies or cells are removed by centrifugation or the like. Subsequently, antifreeze proteins can be isolated and purified from the above culture product through the use of a biochemical method that is generally employed for protein isolation and purification, and specifically through the use of one or an appropriate combination of ammonium sulfate precipitation, gel chromatography, ion exchange chromatography, affinity chromatography, and the like.

Whether or not antifreeze proteins are obtained can be confirmed by SDS-polyacrylamide gel electrophoresis or the like.

Antifreeze proteins or polypeptides having side chains for binding to water molecules on the molecular surfaces of the polypeptides can be immobilized on a carrier according to a method known for immobilizing proteins on a carrier.

Examples of a method employed herein include: a method that uses binding of amino acid residues having affinity for metal ions, such as histidine, cysteine, or tryptophan residues with metal ions; a method that uses binding of cysteine residues with maleimide groups; a method that uses binding of biotin-binding proteins (e.g., avidin or streptavidin) with biotin; a method that uses binding of thioredoxin tags with phenylarsine oxide; a method that uses binding of glutathione-S-transferase with glutathione; a method that uses antigen-antibody binding; a method that uses hydrophobic interaction between a carrier having a hydrophobic surface and proteins; and a method that uses binding of amino groups or carboxyl groups on a carrier with amino groups or carboxyl groups on proteins.

A specific example of a method that uses binding of amino acid residues having affinity for metal ions with metal ions is a method that uses coordinate bonds between histidine tags that are introduced into the above polypeptides or antifreeze proteins and metal ions. A histidine tag means a sequence of several, preferably 3 to 10, and more preferably 6 histidine residues. Histidine tags can be introduced by a known method. A suitable method that involves the use of a vector having a nucleotide sequence that encodes a histidine tag portion. Metal complexes, or preferably, nickel or cobalt complexes are introduced onto a carrier, so that polypeptides or antifreeze proteins having the above histidine tags can be immobilized with high affinity.

Metal complexes can be formed by introducing chelate ligands onto a carrier and then adding metal ions to the carrier. Examples of the structures of chelate ligands include those having structures of iminodicarboxylic acid, nitrilotriacetic acid, terpyridine, bipyridine, triethylenetetramine, biethylenetriamine, ethylenediamine, trimethylenediamine, ethylenediaminetetraacetic acid, diethylenetriamine pentaacetic acid, a macrocyclic polyaminedioxo derivative, sodium pyrophosphate, sodium tripolyphosphate, sodium polyphosphate, tartaric acid, citric acid, gluconic acid, dimethylglyoxime, 2,4-pentanedione, alanine, diaminocyclopentane, diethylenetriamine, dimethylglyoxime, acethylenetriamine pentaacetic acid, glycine, hexaethylenehexamine, 2-methyl-1,2-propanediamine, isoquinoline, malonic acid, O-phenylenediamine, oxalic acid, N,N,N',N'-tetrakis(2-aminoethyl)ethylenediamine, 1,10-phenanthroline, γ-picoline-1,2-propanediamine, pyridine, quinoline, and urea.

Furthermore, thiol groups (of cysteine residues contained in or newly introduced into the above polypeptides or antifreeze proteins) can also be immobilized on a metal carrier based on their affinity for metal ions (Love J. C. et al., Chem. Rev., 105, 1103-1169 (2005)). A carrier made of a metal and a carrier having a metal film on the surface of a substrate (e.g., such as a polymer substrate) that is made of a material other than metal can both be used as a metal carrier. Examples of metals having affinity for thiol groups of cysteine residues include gold, silver, copper, platinum, iridium, nickel, and ruthenium. Preferably, a carrier wherein gold is deposited on a silicon substrate is used. When a metal film is formed on the surface of a substrate, the thickness of the metal film is generally between 100 Å and 2000 Å and preferably between 500 Å and 1000 Å. Moreover, substrates having semiconductors such as $In_2O_3$, CdS, and GaAs or substrates having thin films thereof can also be carriers for binding to thiol groups.

Cysteine residues may be introduced when antifreeze proteins are produced by a known recombination method. Alternatively, cysteine residues may be introduced through chemical binding of the cysteine residues. Cysteine is introduced preferably at the N terminus or the C terminus. For example, introduction can be carried out by causing the N-terminal amino group to react with the carboxyl group of cysteine. Furthermore, the N-terminal amino group is caused to react with the carboxyl group of an appropriate linker such as $N_2H(CH_2)_2O(CH_2)_2OCH_2COOH$ having an amino group and a carboxyl group. The amino group of the linker is then caused to react with the carboxyl group of cysteine, so that cysteine can be bound to the N terminus via the linker.

Alternatively, a compound having a thiol group and an amino or carboxyl group is caused to react with: the above carrier made of a metal; a carrier having a metal film on the surface of a substrate made of a material such as a polymer substrate; or preferably a carrier wherein gold is deposited on a silicon substrate. The amino or carboxyl group can also be introduced onto the carrier surface based on affinity between the thiol group of the compound and the metal. Immobilization can then be carried out by forming peptide bonds between the amino or carboxyl groups and carboxyl or amino groups of polypeptides or antifreeze proteins to be immobilized. When fish-derived type III antifreeze proteins are immobilized, a compound having a thiol group and a carboxyl group (a thiol compound having a carboxyl group) is used. Specifically, peptide bonds are preferably generated between the terminal amino group of an antifreeze protein and the carboxyl group. When carboxyl groups are introduced onto a carrier through the use of a thiol compound having a carboxyl group, the carboxyl groups are preferably subjected to active esterification using a dehydration and condensation agent such as cyanamide or carbodiimide (e.g., 1-[3-(dimethylamino)propyl]-3-ethylcarbodiimide) and a compound such as N-hydroxysuccinimide. With this treatment, a group can be formed wherein an active ester group such as an N-hydroxysuccinimide group is bound to the terminus of a hydrocarbon group via an amide bond. An active ester group is advantageous because of its high reactivity with the amino groups of polypeptides. Examples of an active ester group include a p-nitrophenyl group, a N-hydroxysuccinimide group, a succinimide group, a phthalimido group, and a 5-norbornene-2,3-dicarboxyimide group. In particular, an N-hydroxysuccinimide group is preferable.

Immobilization can also be carried out by causing the formation of covalent bonds between thiol groups (of cysteine residues contained in or newly introduced into the above polypeptides or antifreeze proteins) and maleimide groups (on or introduced onto a carrier). Maleimide groups can be introduced onto a carrier using a known reagent (e.g., Sulfo-EMCS, DOJINDO).

Furthermore, the above polypeptides or antifreeze proteins can also be immobilized on a carrier via antigen-antibody binding using a carrier to which antibodies against the polypeptides or the antifreeze proteins are bound. Moreover, the above polypeptides or the antifreeze proteins can also be immobilized on a carrier which has a hydrophobic surface through interaction with hydrophobic sites of such polypeptides or antifreeze proteins. An example of such carrier having a hydrophobic surface is a monomolecular film wherein alkylthiol molecules (e.g., $HS(CH_2)_{11}CH_3$) are immobilized on a carrier. At this time, such polypeptides or antifreeze proteins into which a plurality of hydrophobic amino acids are introduced can also be used.

In the case of a method that uses binding of biotin-binding proteins such as avidin or streptavidin with biotin, immobilization is carried out by introducing biotin into the above polypeptides or antifreeze proteins and then binding the biotin to biotin-binding proteins bound on a carrier.

In the present invention, polypeptides or antifreeze proteins which have been modified by introduction of biotin as described above, for example, are also encompassed in the scope of the polypeptides having side chains for binding to water molecules on the molecular surfaces of the polypeptides or the antifreeze proteins.

Alternatively, methods that can also be used herein are: a method (active ester method) that involves causing carboxyl groups of a carrier to react with N-hydroxy succinimide to convert the groups into succinimideoxycarbonyl groups and then causing the reaction with the above polypeptides or antifreeze proteins to take place at their amino group portions; and a method (condensation method) that involves causing a condensation reaction to take place between the amino or carboxyl groups of a carrier and the carboxyl or amino groups of the above polypeptides or antifreeze proteins in the presence of a condensing reagent such as dicyclohexylcarbodiimide. Here, preferably, the amino or carboxyl groups of the polypeptides or the antifreeze proteins, which are present on the molecular surfaces of the polypeptides or the proteins, are caused to react with functional groups on a carrier.

Furthermore, methods that can also be used herein are: a method (carrier-crosslinking method) that involves crosslinking a carrier and the above polypeptides or antifreeze proteins using a compound having 2 or more functional groups, such as glutaraldehyde; and a method that involves immobilizing the polypeptides or the antifreeze proteins on the surface of a carrier via a silane coupling agent having an epoxy group.

A carrier on which the above polypeptides or antifreeze proteins are immobilized is not limited, as long as it can carry the polypeptides or the antifreeze proteins without damaging their functions. A carrier can be appropriately selected by persons skilled in the art according to the immobilization method to be employed.

Examples of materials for such carrier include conductive materials such as metals (e.g., platinum, platinum black, gold, palladium, rhodium, silver, mercury, tungsten, or compounds thereof) and carbon represented by graphite and carbon fiber; silicon materials represented by single crystal silicon, amorphous silicon, silicon carbide, silicon oxide, and silicon nitride, for example, and composite materials of these silicon materials represented by SOI (silicon on insulator); inorganic materials such as glass, quartz glass, alumina, sapphire, ceramics, forsterite, and photosensitive glass; and organic materials such as polyethylene, ethylene, polypropylene, cyclic polyolefin, polyisobutylene, polyethylene terephthalate, unsaturated polyester, fluorine-containing resin, polyvinyl chloride, polyvinylidene chloride, polyvinyl acetate, polyvinyl alcohol, polyvinyl acetal, acryl resin, polyacrylonitrile, polystyrene, acetal resin, polycarbonate, polyamide, polyacrylamide, phenol resin, urea resin, epoxy resin, melamine resin, styrene acrylonitrile copolymer, acrylonitrile butadiene-styrene copolymer, polyphenylene oxide, polysulfone, cellulose, dextran, chitin, collagen, and amino acid polymer. The form of the carrier is not particularly limited. For example, a carrier may be in the form of a vessel, a substrate, a porous carrier, or beads (nano- to macroparticles).

Antifreeze proteins are preferably oriented and immobilized on a carrier, so that their sites for binding to ice crystals are exposed. In this manner, antifreeze proteins can be integrated with the crystal-binding sites being exposed on the carrier surface, so that a carrier upon which antifreeze proteins are immobilized having high ice nucleation activity and high activity to promote freezing can be obtained. The phrase "oriented . . . so that their sites for binding to ice crystals are exposed" means that the sites for binding to ice crystals are oriented facing the outside of the carrier, facilitating their contact with water or a hydrous substance.

When antifreeze proteins or polypeptides having side chains for binding to water molecules on the molecular surfaces of the polypeptides are oriented and immobilized on a carrier, their three-dimensional structure is taken into consideration. Specifically, suitable carrier-binding sites in the above polypeptides or antifreeze proteins are selected or introduced based on the immobilization method employed. In the three-dimensional structure of the above polypeptides or antifreeze proteins, carrier-binding sites are selected or introduced, so that the carrier-binding sites are present on the side opposite to the side chains for binding to water molecules or the sites for binding to ice crystals.

For example, when the antifreeze proteins comprising the amino acid sequence of SEQ ID NO: 2 or proteins functionally equivalent thereto are immobilized on a carrier, cysteine is introduced at their amino termini and then the resultants are immobilized on a metal carrier, preferably a gold carrier, or a carrier having gold on its surface. Thus, the antifreeze proteins are oriented and immobilized on the carrier so that their sites for binding to ice crystals are exposed. The amino acid sequence of the antifreeze protein comprising the amino acid sequence of SEQ ID NO: 2, wherein cysteine is introduced at the amino terminus and the nucleotide sequences of the DNA encoding the same are shown in SEQ ID NOS: 4 and 3, respectively.

The freezing of water or a hydrous substance can be promoted by causing the carrier upon which polypeptides are immobilized and the carrier upon which antifreeze proteins are immobilized of the present invention to come into contact with water or a hydrous substance. Furthermore, water or a hydrous substance can be frozen while gases dissolved in the water or the hydrous substance are removed. As a result, clear ice can be produced. Furthermore, water (or a water component) can be frozen while components other than water in a hydrous substance are removed. As a result, such components other than water in the hydrous substance can be concentrated.

In the present invention, "hydrous substance" means a substance that contains water molecules and molecules other than such water molecules. Examples of such hydrous substance include: aqueous solutions comprising solutes and solvents; mixtures of substances that are insoluble in water and water; foods such as cereals, noodles, eggs, vegetables, fruits, meat, seafood, bread dough, frozen sweets, and processed foods; medical products; diagnostic drugs; reagents; cosmetic products; toilet water; blood; serum; blood platelets; sperms; ova; single-cell; multi-cell; living tissues; organs such as the heart, pancreas, liver, and kidney and stock solutions thereof; snow melting agents; and anti-frost agents.

The phrase "promoting the freezing of water or a hydrous substance" means to raise the freezing temperature (freezing point) of the water or the hydrous substance. It is thought that polypeptides or antifreeze proteins integrated on the carrier in the present invention cause the formation of ice nuclei through promotion of integration of multiple water molecules, and thus promote the freezing of water or a hydrous substance. In general, water freezes at approximately −20° C. Through contact with the carrier upon which polypeptides are immobilized and the carrier upon which antifreeze proteins are immobilized of the present invention, the freezing temperature of water can be raised to approximately −2° C.

The present invention enables the freezing of water or a hydrous substance with the use of less cooling energy than is required in conventional cases. The use of the carrier upon which polypeptides are immobilized and the carrier upon which antifreeze proteins are immobilized of the present invention for ice making tanks, ice trays, wrapping films, and the like is expected. The use of these carriers cuts out the conventional need for lowering freezer temperature to a range between −20° C. and −196° C., so that large reductions in energy costs can be expected.

The present invention will be further described by referring to the following examples. However, the present invention is not limited by the scope of these examples.

EXAMPLES

(1) Preparation of Natural Antifreeze Protein

Fish-derived type III antifreeze protein (AFP) was prepared from the fish body paste of fish of the genus *Zoarces* (*Nagakaji: Zoarces elongatus Kner*) according to the method described in JP Patent Publication (Kokai) 2004-083546 A. The amino acid sequence (SEQ ID NO: 2) and the nucleotide sequence (SEQ ID NO: 1) of DNA encoding the antifreeze protein of the fish-derived type III antifreeze protein used herein are shown in the sequence listing.

(2) Preparation of Antifreeze Protein (Cys-AFP) into which Cysteine is Introduced (a) Construction of expression vector A DNA primer encoding 6 amino acids at the amino terminus of the fish-derived type III antifreeze protein (AFP) was chemically synthesized, into which a Cys codon (TGC) had been inserted immediately following the initiation codon (ATG). A DNA primer encoding the carboxy terminus and the termination codon of the antifreeze protein was chemically synthesized. Next, PCR was carried out using the thus synthesized primers and a DNA encoding the antifreeze protein as a template. The amplified DNA fragment was digested with restriction enzymes Nde I and Xho I and then incorporated into a pET20b vector (pETCys-AFP) that had been digested with the same enzymes. The nucleotide sequence (SEQ ID NO: 3) of a DNA for introduction of cysteine into the amino terminus of the fish-derived type III antifreeze protein and the amino acid sequence (SEQ ID NO: 4) expressed based on the DNA are shown in the sequence listing.

(b) Cys-AFP Expression by *Escherichia coli*

*Escherichia coli* BL21 (DE3) was transformed using the plasmid pETCys-AFP. Since an ampicillin resistance gene had been introduced into the plasmid pETCys-AFP, transformants were selected by spreading *Escherichia coli* over LB agar medium containing 100 μg/ml ampicillin and then incubating the *E. coli* overnight at 28° C. One of the thus formed colonies was inoculated in 2 ml of LB medium containing 100 μg/ml ampicillin, followed by overnight culture at 28° C. The culture solution was subcultured in 100 ml of LB medium containing 100 μg/ml ampicillin, followed by overnight culture at 28° C. Of 100 ml of the culture solution, 20 ml of the culture solution was subcultured in 2000 ml of LB medium containing 100 μg/ml ampicillin, followed by culture at 28° C. while monitoring the absorbance at the wavelength of 600 nm indicating the degree of the growth of *Escherichia coli*. When the absorbance at the wavelength of 600 nm reached 0.5, isopropyl-β-D(−)-thiogalactoside was added to a final concentration of 0.5 mM, so as to induce the expression of Cys-AFP. Culture was further carried out for 8 hours.

(c) Cys-AFP Purification

The culture solution was subjected to 15 minutes of centrifugation at 3600×g and 4° C., and then microbial bodies were collected. The microbial bodies were suspended in a 10 mM Tris-hydrochloride buffer/1 mM disodium ehylenediaminetetraacetate (pH 8.0) (TE buffer) and then disrupted in ice by ultrasonication. The resultant was subjected to 30 minutes of centrifugation at 11900×g and 4° C. so that the resultant was separated into a soluble fraction and an insoluble fraction. The soluble fraction was subjected to dialysis against a 50 mM sodium citrate buffer (pH 2.9), thereby carrying out substitution of the solution. The precipitate generated by dialysis was removed via 30 minutes of centrifugation at 11900×g and 4° C., so that a supernatant liquid was collected. For purification of Cys-AFP from the supernatant liquid, a DUO Flow system (BIO-RAD) to which an High-S column (BIO-RAD) equilibrated with a 50 mM sodium citrate buffer (pH 2.9) had been connected was used. First, the supernatant liquid was applied to the column and then the column was washed with a buffer A (50 mM sodium citrate buffer (pH 2.9)) in a volume 3 times greater than that of the column. Next, the buffer A was applied to the column while the mixing ratio of a buffer B (50 mM sodium citrate buffer, 1 M sodium chloride (pH 2.9)) was increased at a constant rate, so that Cys-AFP was eluted. Elution of Cys-AFP was detected with absorbances at wavelength of 280 nm and 214 nm. Eluted Cys-AFP was collected using a fraction collector. Purification was always carried out within a chamber at 4° C. Fluid velocity employed herein was determined to be 1 ml/min. The collection amount per fraction was determined to be 1 ml.

(d) Sodium Dodecyl Sulfate-Polyacrylamide Gel Electrophoresis

According to general procedures, purified Cys-AFP was electrophoresed with 15% polyacrylamide gel using an electrophoresis apparatus (ATTO). To measure molecular weights, Broad Range SDS-PAGE Standard (BIO-RAD) was simultaneously electrophoresed. A sample buffer containing a 0.065 M Tris-hydrochloride buffer (pH 6.8), 2% sodium dodecyl sulfate, 10% sucrose, 5% β-mercaptoethanol, and 0.001% bromophenol blue was used. A concentrate gel was prepared by mixing 0.75 ml of a 0.5 M Tris-hydrochloride buffer (pH 6.8), 0.45 ml of a mixture of 30% acrylamide and bis (37.5:1), 0.12 ml of 10% sodium dodecyl sulfate, and 1.78 ml of distilled water. A separation gel was prepared by mixing 2.25 ml of 1.5 M Tris-hydrochloride buffer (pH 8.8), 4.5 ml of a mixture of 30% acrylamide and bis (37.5:1), 0.36 ml of 10% sodium dodecyl sulfate, and 1.89 ml of distilled water. A buffer for electrophoresis used herein was prepared by dissolving 3.03 g of tris(hydroxymethyl)aminomethane, 14.4 g of glycine, and 1 g of sodium dodecyl sulfate in a total of 1 liter of distilled water. Gel staining was carried out overnight using a stain solution prepared by dissolving 20 ml of methanol, 12.5 g of ammonium sulfate, 2.5 ml of phosphoric acid, and 0.04% Coomassie brilliant blue G-250 in 100 ml of a distilled water. Resultants were then destained with distilled water. A single band of Cys-AFP with a molecular weight of 7 KDa and the same for the dimer thereof were observed, so that the purification of Cys-AFP with high purity could be confirmed.

(3) Determination of Antifreeze Activity

The natural AFP prepared in (1) and Cys-AFP prepared in (2) were subjected to dialysis against a 50 mM phosphate buffer and a 0.05 M NaCl aqueous solution (pH 6.0), and buffer substitution was carried out. Subsequently, the resultants were concentrated by ultrafiltration to a concentration of 1 mg/ml. Whether or not a sample solution of interest has an antifreeze activity can be evaluated by carrying out an experiment of observing bi-pyramidal ice crystals under a low temperature microscope using only 1 μl of the solution.

1 μl of the sample solution prepared as described above was placed dropwise on a cover glass with a diameter of 16 mm of a DMLB100 photomicroscope (manufactured by Leica Microsystems AG). The sample was placed between this cover glass and another cover glass with a diameter of 12.5 mm, and set in a cooler box provided at the stage part of the DMLB100 photomicroscope. Holes with a diameter of 1 mm were made on the top and on the bottom of the cooler box for lighting, so that light from the light source of the photomicroscope entered the hole on the bottom, passed through the inside of the box and the hole on the top, and thus entered the lens. The sample solution was set on the optical axis specified by the holes on the top and on the bottom, so that substances in the sample solution on the optical axis could be observed under a microscope. The temperature within the cooler box wherein the sample solution was set was controlled by an LK600 temperature controller (manufactured by Linkam) with an error range of +/−0.1° C. When the sample solution was set at room temperature, the temperature within the cooler box was lowered by 0.2° C. every second to −22° C. using the temperature controller. The entire sample solution froze at temperatures somewhere between approximately −14° C. and −22° C. After freezing, the temperature within the cooler box was raised by 0.2° C. every second, and this was stopped at 0° C. When the temperature had been maintained at −3° C. for approximately 1 to 10 seconds, the frozen solution started to defreeze, and experienced an ice crystal state with numerous cracks. Then, ice crystals floating in water were observed. At this moment, the temperature within the cooler box was lowered to approximately −2° C. to 3° C., the lowering of the temperature was stopped, and then the shapes of the ice crystals were observed. Bi-pyramidal ice crystals were observed in the cases of the natural AFP and Cys-AFP used in this experiment, confirming that all of these proteins had antifreeze activity.

(4) Orientation and Immobilization onto Gold Substrate (a) Immobilization of Natural AFP A gold thin film substrate prepared by deposition of gold with a thickness of 500 Å on a silicon wafer (111) was immersed overnight in an ethanol solution of 0.1 mM mercaptopropionic acid. An interface was prepared on which propionic acid groups were exposed with the use of the bonds between the thiol groups of mercaptopropionic acid and gold. The carboxyl groups of propionic acid on the interface were immersed at 25° C. for 1 hour in a mixed solution of 2 mM carbodiimide and 5 mM succinimide in 100 mM phosphate buffer (pH 7.0) for activation. The resultant was then immersed overnight at 4° C. in a natural AFP solution (10 mM phosphate buffer (pH 8.0)). Antifreeze proteins were immobilized on the gold thin film with the use of peptide condensation between the activated carboxyl groups and the amino groups of the natural AFPs; that is, the N-terminal amino groups, which were thought to be exposed to the solvent to the highest extent and have high reactivity.

(b) Immobilization of Cys-AFP

A gold thin film substrate prepared by deposition of gold with a thickness of 500 Å on a silicon wafer (111) was immersed overnight at 25° C. in a 0.1 mM Cys-AFP solution (50 mM phosphate buffer and 0.05 M NaCl aqueous solution (pH6.0)). Antifreeze proteins were immobilized on the gold thin film with the use of bonds between the thiol groups of cysteine residues and gold.

(5) Evaluation of Surface Upon which Antifreeze Proteins Had been Immobilized

The carrier upon which antifreeze proteins had been immobilized by this method was analyzed by X-ray photoelectron spectroscopy, reflection infrared spectrometry, surface enhanced infrared spectrometry, electrochemical analysis, and a quartz crystal microbalance method.

In XPS analysis, significantly increased quantities of nitrogen and carbon atoms were observed before and after immobilization. Furthermore, signal generation resulting from a gold-sulfur bond was observed. In electrochemical analysis and QCM analysis, the quantity of antifreeze proteins immobilized was estimated to be approximately $5 \times 10^{-11}$ mol/cm$^2$. That is a monomolecular film level. In infrared spectroscopic measurement, orientation and immobilization of the antifreeze proteins were suggested based on signals of amide I and amide II.

Figure 1:
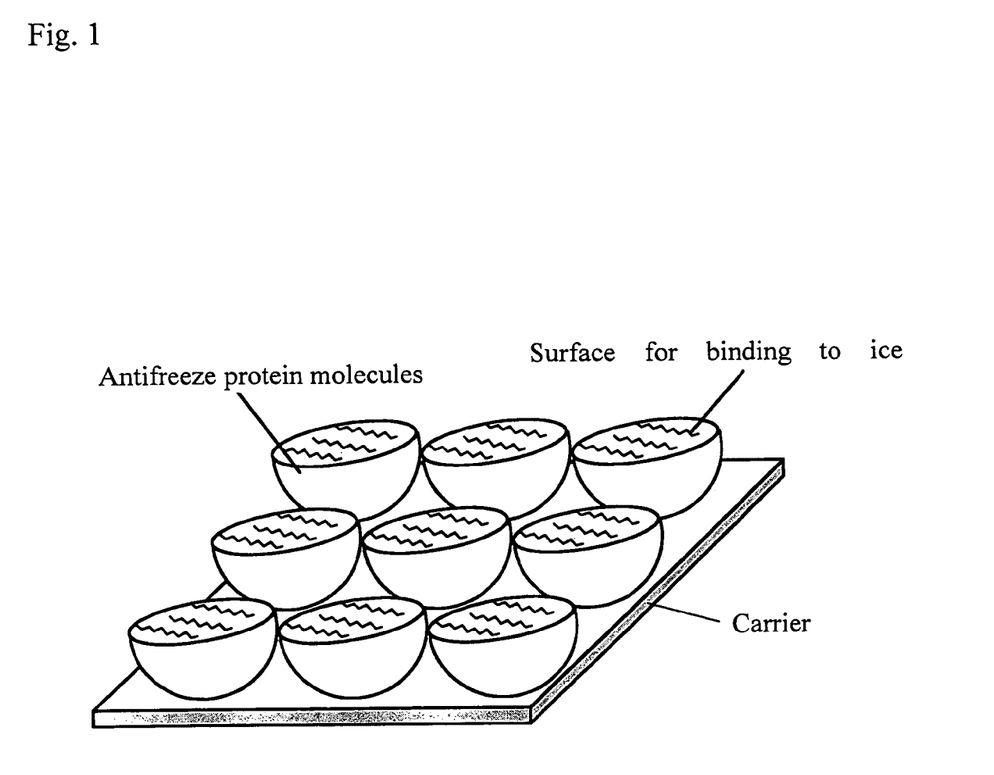
FIG. 1 is a schematic diagram showing the structure of a carrier upon which antifreeze proteins are immobilized of the present invention.

As described above, the quantity of the antifreeze proteins immobilized was confirmed. Furthermore, it was confirmed that the antifreeze proteins had been immobilized on the substrate surface via thiolate bonds or peptide bonds (in this case, a thiol compound having a carboxyl group was used as a spacer) and that the sites for binding to ice crystals of the antifreeze proteins were oriented, integrated, and immobilized on the carrier (FIG. 1).

(6) Experiment for Evaluation of the Activity to Promote Freezing of the Carrier Upon which Antifreeze Proteins Had been Immobilized The following experiment was conducted for evaluating the activity to promote freezing of the substrate upon which antifreeze proteins had been immobilized.

Figure 2:
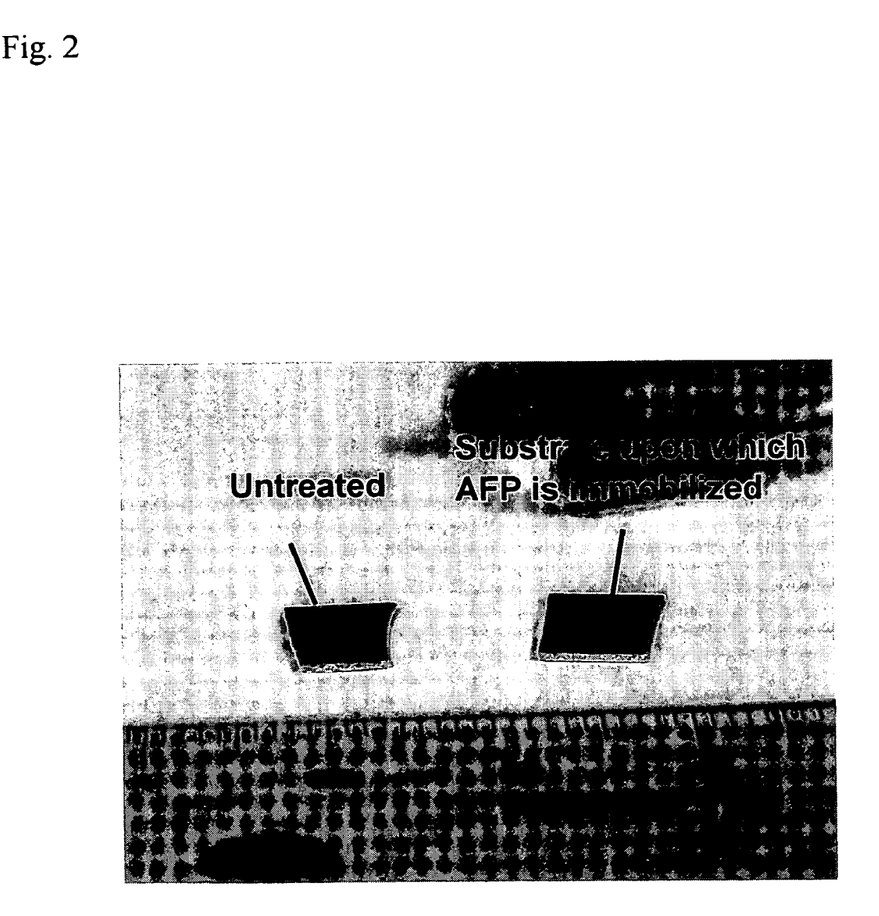
FIG. 2 shows a gold thin film substrate (left: untreated with AFP) prepared by deposition of gold on a silicon wafer (111) with a thickness of 500 Å and a substrate (right: substrate upon which AFP was immobilized) prepared by immobilizing Cys-AFP on the gold-deposited substrate.
Figure 3:
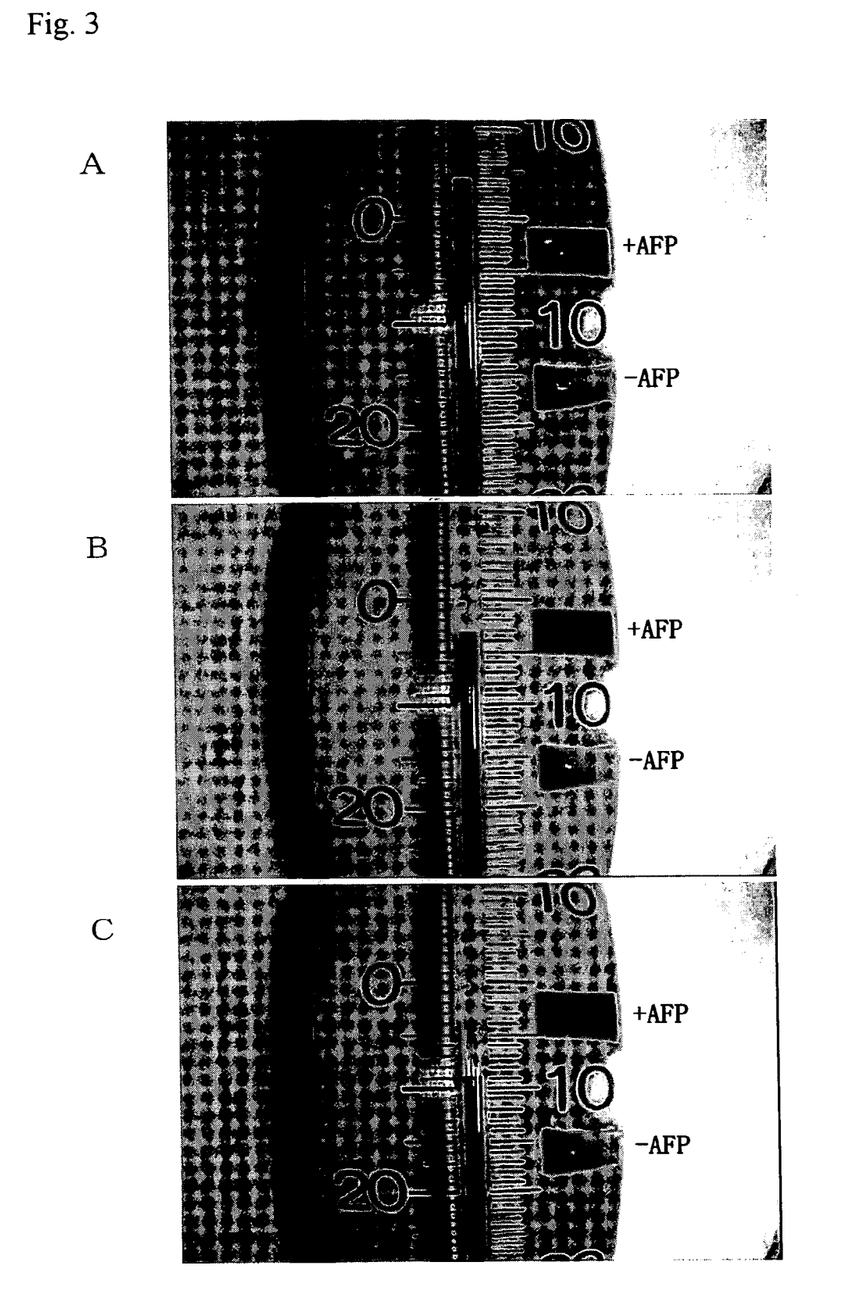
FIG. 3 shows some of successive images showing the manner in which water froze and underwent sublimation when 2 µl of water droplets were allowed to stand on a substrate which had been untreated with AFP and on a substrate upon which AFP had been immobilized which are shown in FIG. 2, following which the temperature was changed from room temperature to −10° C. at a rate of approximately 0.7° C./minute. "A" is the image obtained at approximately 4° C., "B" is the image obtained at approximately −3° C., and "C" is the image obtained at approximately −9° C.

At the beginning, water droplets (2 μl each) of distilled water were added to and allowed to stand on a +AFP substrate upon which antifreeze proteins had been immobilized and a −AFP substrate upon which no antifreeze proteins had been immobilized (see FIG. 2). Next, these substrates were allowed to stand on a thermometer placed within a low temperature incubator LTI-601SD (produced by EYELA). A fiber video camera was placed so that the temperature of the thermometer and two substrates came within the visual field simultaneously. An iPLEX MX videoscope system (produced by OLYMPUS) was used as a video camera. The temperature of the incubator was set at −10° C. and then the switch for starting a temperature decline was turned on. Thus, the temperature within the incubator was lowered from room temperature to −10° C. at approximately 0.7° C./minute. The manner in which the water droplets that had been allowed to stand on the 2 substrates froze and underwent sublimation as temperature fell within the incubator was recorded using a DR-MX1 recording system (manufactured by VICTOR). Through examination of the images played at low speed, the freezing temperature (freezing point) of the water droplets of each case was determined. FIG. 3 shows some of played images obtained in this experiment.

"A" is the image obtained at approximately 4° C., "B" is the image obtained at approximately −3° C., and "C" is the image obtained at approximately −9° C. This experiment revealed that the water droplets on the +AFP substrate froze at −2.5° C. while the water droplets on the −AFP substrate froze at −10° C. The above results suggested that the substrate on which the antifreeze proteins had been immobilized had activity to promote freezing higher than that of the substrate upon which no antifreeze proteins had been immobilized.

When a similar experiment was conducted under conditions in which no water droplets underwent sublimation, water droplets on the +AFP substrate upon which the antifreeze proteins had been immobilized gradually froze (the freezing begun from the portion that was in contact with the substrate interface) at a temperature between −0.5° C. and −2.5° C., forming clear ice. In the meantime, water droplets on the −AFP substrate upon which no antifreeze proteins had been immobilized instantly froze at a temperature near −11° C., forming cloudy (milky) ice.

The present inventors succeeded in orientation and immobilization of antifreeze proteins where specific amino acids located on the side opposite to the sites for binding to ice crystals of the antifreeze proteins were bound to a carrier. Namely, the present inventors succeeded in integration of the sites for binding to ice crystals of the antifreeze proteins. The present inventors discovered that the integrated sites for binding to ice crystals exert very high ice nucleation activity and very high activity to promote freezing.

All publications, patents, and patent applications cited herein are incorporated herein by reference in their entirety.

INDUSTRIAL APPLICABILITY

Applications of the present invention are expected for the manufacturing industry, the processing industry, the freezing industry, the ice-making industry, the thermal preservation industry, food preservation technology, cell preservation technology, organ preservation technology, artificial snowfall technology, and rainmaking technology, for example.

What is claimed is:

1. A method for promoting the freezing of water or a hydrous substance, which is carried out by integrating and immobilizing fish-derived type III antifreeze proteins on a carrier, and causing the carrier upon which antifreeze proteins are immobilized to come into contact with water or a hydrous substance, thereby promoting freezing of the water or the hydrous substance.

2. A method for freezing water or a hydrous substance while removing a gas contained in the water or the hydrous substance, which is carried out by integrating and immobilizing fish-derived type III antifreeze proteins on a carrier, and causing the carrier upon which antifreeze proteins are immobilized to come into contact with the water or the hydrous substance, thereby freezing the water or the hydrous substance while removing a gas contained in the water or the hydrous substance.

3. A method for freezing a water component in a hydrous substance while concentrating components other than water in the hydrous substance, which is carried out by integrating and immobilizing fish-derived type III antifreeze proteins on a carrier, and causing the carrier upon which antifreeze proteins are immobilized to come into contact with the hydrous substance, thereby freezing the water component in the hydrous substance while concentrating components other than water in the hydrous substance.

4. The method according to claim 1, wherein the fish-derived type III antifreeze protein is type III antifreeze protein derived from Zoarces elongatus Kner comprising SEQ ID NO: 2 with a cysteine on the N-terminus.

5. The method according to claim 1, wherein the carrier comprises a gold substrate.

6. The method according to claim 5, wherein the carrier comprises a gold substrate.

* * * * *

UNITED STATES PATENT AND TRADEMARK OFFICE
CERTIFICATE OF CORRECTION

| | |
|---|---|
| PATENT NO. | : 7,700,718 B2 |
| APPLICATION NO. | : 11/635058 |
| DATED | : April 20, 2010 |
| INVENTOR(S) | : Yasuhiro Mie et al. |

It is certified that error appears in the above-identified patent and that said Letters Patent is hereby corrected as shown below:

Column 22, line 59:
In claim 6 delete "5" and insert --4--.

Signed and Sealed this
Twenty-eighth Day of February, 2012

David J. Kappos
*Director of the United States Patent and Trademark Office*

SEQUENCE LISTING

```
<160> NUMBER OF SEQ ID NOS: 4

<210> SEQ ID NO 1
<211> LENGTH: 201
<212> TYPE: DNA
<213> ORGANISM: Zoarces elongatus Kner
<220> FEATURE:
<221> NAME/KEY: CDS
<222> LOCATION: (1)..(201)

<400> SEQUENCE: 1 atg aac cag gag tcc gtg gta gcc gcc gtt ctg atc ccc ata aat act        48
Met Asn Gln Glu Ser Val Val Ala Ala Val Leu Ile Pro Ile Asn Thr
  1               5                  10                  15 gcc ctg act gtg ggg atg atg acg aca cgg gtg gtc tcc cca acg ggc        96
Ala Leu Thr Val Gly Met Met Thr Thr Arg Val Val Ser Pro Thr Gly
             20                  25                  30 atc ccc gcc gag gac att ccc cga tta atc tca atg caa gtg aac cag      144
Ile Pro Ala Glu Asp Ile Pro Arg Leu Ile Ser Met Gln Val Asn Gln
         35                  40                  45 gta gtg ccg atg ggc aca acc ctc atg cca gac atg gtg aaa ggg tac      192
Val Val Pro Met Gly Thr Thr Leu Met Pro Asp Met Val Lys Gly Tyr
     50                  55                  60 gcc ccg gct                                                          201
Ala Pro Ala
 65

<210> SEQ ID NO 2
<211> LENGTH: 67
<212> TYPE: PRT
<213> ORGANISM: Zoarces elongatus Kner

<400> SEQUENCE: 2

Met Asn Gln Glu Ser Val Val Ala Ala Val Leu Ile Pro Ile Asn Thr
  1               5                  10                  15

Ala Leu Thr Val Gly Met Met Thr Thr Arg Val Val Ser Pro Thr Gly
             20                  25                  30

Ile Pro Ala Glu Asp Ile Pro Arg Leu Ile Ser Met Gln Val Asn Gln
         35                  40                  45

Val Val Pro Met Gly Thr Thr Leu Met Pro Asp Met Val Lys Gly Tyr
     50                  55                  60

Ala Pro Ala
 65

<210> SEQ ID NO 3
<211> LENGTH: 204
```

-continued

```
<212> TYPE: DNA
<213> ORGANISM: Artificial Sequence
<220> FEATURE:
<223> OTHER INFORMATION: Description of Artificial Sequence:
      Cys-Anti-freeze protein
<220> FEATURE:
<221> NAME/KEY: CDS
<222> LOCATION: (1)..(204)

<400> SEQUENCE: 3 atg tgc aac cag gag tcc gtg gta gcc gcc gtt ctg atc ccc ata aat        48
Met Cys Asn Gln Glu Ser Val Val Ala Ala Val Leu Ile Pro Ile Asn
 1               5                  10                  15 act gcc ctg act gtg ggg atg atg acg aca cgg gtg gtc tcc cca acg        96
Thr Ala Leu Thr Val Gly Met Met Thr Thr Arg Val Val Ser Pro Thr
                20                  25                  30 ggc atc ccc gcc gag gac att ccc cga tta atc tca atg caa gtg aac       144
Gly Ile Pro Ala Glu Asp Ile Pro Arg Leu Ile Ser Met Gln Val Asn
            35                  40                  45 cag gta gtg ccg atg ggc aca acc ctc atg cca gac atg gtg aaa ggg       192
Gln Val Val Pro Met Gly Thr Thr Leu Met Pro Asp Met Val Lys Gly
         50                  55                  60 tac gcc ccg gct                                                        204
Tyr Ala Pro Ala
 65

<210> SEQ ID NO 4
<211> LENGTH: 68
<212> TYPE: PRT
<213> ORGANISM: Artificial Sequence
<220> FEATURE:
<223> OTHER INFORMATION: Description of Artificial Sequence:
      Cys-Anti-freeze protein

<400> SEQUENCE: 4

Met Cys Asn Gln Glu Ser Val Val Ala Ala Val Leu Ile Pro Ile Asn
 1               5                  10                  15

Thr Ala Leu Thr Val Gly Met Met Thr Thr Arg Val Val Ser Pro Thr
                20                  25                  30

Gly Ile Pro Ala Glu Asp Ile Pro Arg Leu Ile Ser Met Gln Val Asn
            35                  40                  45

Gln Val Val Pro Met Gly Thr Thr Leu Met Pro Asp Met Val Lys Gly
         50                  55                  60

Tyr Ala Pro Ala
 65
```